(12) United States Patent
Flohr et al.

(10) Patent No.: US 7,187,745 B2
(45) Date of Patent: Mar. 6, 2007

(54) METHOD AND APPARATUS FOR PRODUCING A COMPUTED TOMOGRAPHY IMAGE OF A PERIODICALLY MOVING ORGAN

(75) Inventors: Thomas Flohr, Uehlfeld (DE); Klaus Klingenbeck-Regn, Nuremberg (DE); Bernd Ohnesorge, Erlangen (DE); Rainer Rienmueller, Graz (AT)

(73) Assignee: Siemens Aktiengesellschaft, Munich (DE)

( * ) Notice: Subject to any disclaimer, the term of this patent is extended or adjusted under 35 U.S.C. 154(b) by 77 days.

(21) Appl. No.: 10/675,302

(22) Filed: Sep. 30, 2003

(65) Prior Publication Data

US 2004/0120450 A1    Jun. 24, 2004

(30) Foreign Application Priority Data

Sep. 30, 2002    (DE) ................................ 102 45 943

(51) Int. Cl.
*A61B 6/00*    (2006.01)
(52) U.S. Cl. ............................. 378/8; 378/62; 600/428
(58) Field of Classification Search .................... 378/8, 378/95, 4, 15, 62, 901; 600/425, 428
See application file for complete search history.

(56) References Cited

U.S. PATENT DOCUMENTS

| | | | | |
|---|---|---|---|---|
| 4,206,363 | A * | 6/1980 | Hounsfield et al. | 378/8 |
| 6,381,487 | B1 * | 4/2002 | Flohr et al. | 600/425 |
| 6,504,893 | B1 * | 1/2003 | Flohr et al. | 378/8 |
| 6,650,726 | B2 * | 11/2003 | Sembritzki et al. | 378/8 |

* cited by examiner

*Primary Examiner*—Courtney Thomas
(74) *Attorney, Agent, or Firm*—Schiff Hardin LLP

(57) ABSTRACT

In a method and device for, generating computed tomography images of a periodically moving organ of an organism, the organ having regions with rest phases and movement phases and the rest phases of different regions ensuing at different points in time, an x-ray source is moved around the body of the organism to be examined to generate projections serving for the image generation during at least one rotation of the x-ray source around the subject to be examined and during a duration that is at least equal to a period of the motion. The projection data are analyzed as to whether the data were acquired during a rest phase or movement phase of a respective region of interest of the organ, and an image of the organ is reconstructed using only data acquired during a rest phase of a respective region of interest of the organ.

16 Claims, 4 Drawing Sheets

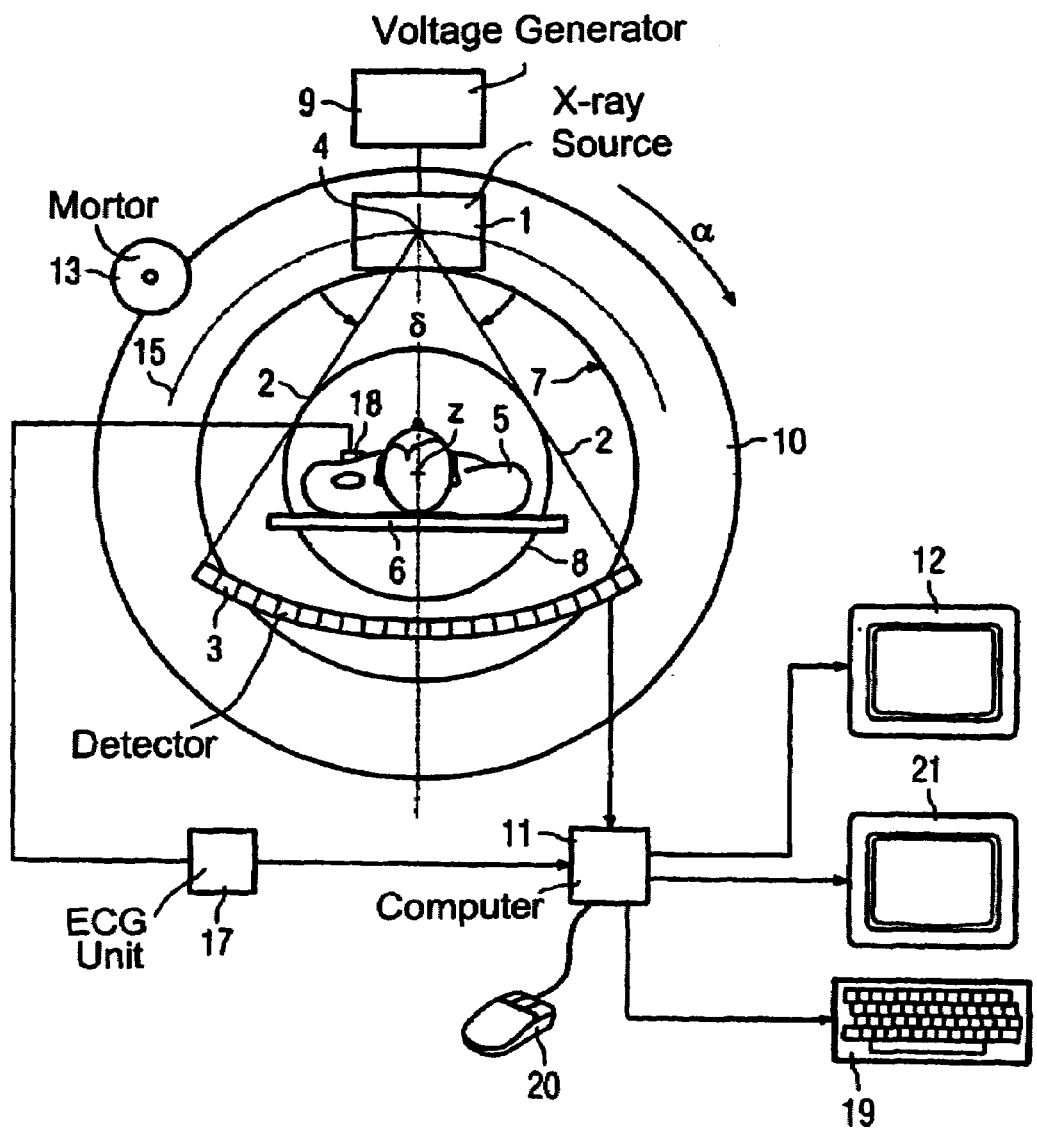

METHOD AND APPARATUS FOR PRODUCING A COMPUTED TOMOGRAPHY IMAGE OF A PERIODICALLY MOVING ORGAN

BACKGROUND OF THE INVENTION

1. Field of the Invention

The present invention concerns a method and computed tomography (CT) apparatus for operating images of a periodically moving organ of an organism, the organ having regions with rest and movement phases with the rest phases of different regions ensuing at different points in time. The method and CT apparatus are of the type wherein an x-ray source is moved around the body of the organism to be examined to the CT images, to obtain a number of projections serving for the image generation during at least one rotation of the x-ray source around the subject to be examined and during a duration that is at least equal to a period of the motion.

2. Description of the Prior Art

Methods and systems of the type described above are used to generate computed tomography images of the heart that show the heart in a rest phase.

By means of such known methods, it is generally not possible to develop computed tomography images of the coronary arteries that contain little movement artifacts, that are useful for the determination of the degree of calcification or the diagnosis of stenoses in the coronary arteries. The regions of the heart that must be imaged for such examinations in computed tomography images lacking movement artifacts are the right coronary artery (RCA), the left aorta (LM=Left Main), left arterial circumflex (LCX) and the left descending artery (LAD=Left Artery Descendent). For the four cited regions, the speed and the phase of the spatial movement are respectively different during a heart cycle.

Since the position of the diastolic phase of the heart can be evaluated, for example from an ECG signal of the patient acquired during the examination, and the ventricles as well as LM and LAD are largely at rest during diastole, it is a common procedure to acquire ECG-triggered axial scan data for representations of the heart lacking movement artifacts. In addition, it is known to first acquire data and to simultaneously record the ECG signal with the data acquisition, in order to then retrospectively determine, using the ECG signal, the data that were acquired during diastole, and to reconstruct an image based on this data.

The reconstruction of an image of the heart based on data that was determined during diastole, however, in general allows no sharp imaging of RCA and LCX, since their movement in the diastole can be significant. Only with electron beam computed tomography (EBT) (due to the short scan times per slice (looms) with these devices) can a measurement interval sometimes be found in a phase of the heart cycle during which the four cited arteries exhibit only little motion. For patients with higher pulse rates, this does not work for the most part. With conventional computed tomography devices common today, that employ scan times of not less than 330 ms per slice, it is impossible, for patients with lower pulse rates to find a measurement interval in which all cited regions exhibit relatively little motion.

SUMMARY OF THE INVENTION

An object of the present invention is to provide a method of the type initially described wherein it is possible to generate computed tomography images lacking movement artifacts with regard to a desired region. A further object of the invention is to provide a computed tomography apparatus to implement such a method.

According to the invention, this object is achieved in a method to generate computed tomography images of a periodically moving organ of an organism (the organ having regions with rest or movement phases with the rest phases of different regions of the organ ensue at different points in time) by moving an x-ray source around the body of the organism to be examined to generate the computed tomography images, including the steps of acquiring a number of projections serving for image generation during at least one rotation of the x-ray source around the subject to be examined and during a duration that is at least equal to one period of the movement, analyzing the data corresponding to the projections as to whether the data were acquired during a rest phase or a movement phase of a respective region of interest of the organ, and reconstructing of an image of the organ using only data acquired during a rest phase of the respective region of interest of the organ.

It is possible with the inventive method to generate computed tomography images of the organ that show regions of the organ in their rest phase. Thus it is possible in the case of the heart to show all arteries of interest in their respective rest phases. With the computed tomography images, reconstructed if necessary in different heart phases, an overall diagnosis is possible for all arteries using the images showing the individual arteries in their rest phases. The required projections can be acquired, for example, from a spiral scan that is recorded by a computed tomography device that having a detector system with one or more rows of detector elements.

In an embodiment of the invention, the analysis of the projection data is undertaken for a number of regions of the organ to determine whether they were acquired during a rest phase or a movement phase of the respective region, and for each region of interest of the organ an image of the organ is reconstructed using only data acquired during a rest phase of the respective region of interest of the organ, and an image including all regions of interest of the organ in their respective rest phase is developed from the images representing the rest phase of the individual regions of interest of the organ. The image acquired in this manner thus shows all regions of interest, for example the four arteries of the heart cited above, in their respective rest phases and thus provides information that would otherwise not be available in a single image.

In order to be able to recognize the data that were acquired during a rest phase and the data acquired during a movement phase of a region of interest of the organ, according to the invention movement artifacts are detected for an image region showing a region of interest of the organ in a sequence of rapidly successive test images. Data acquired during a rest phase of the respective region of interest of the organ that have contributed to a test image will form a portion of the test image that is substantially free of movement artifacts in the image region showing the respective region of interest of the organ. The detection of movement artifacts can ensue in which line artifacts and/or double contours are considered to be an indication of movement artifacts. However, the detection of movement artifacts also can ensue using difference images acquired from subtraction of successive test images. In order to have the required test images available quickly, their reconstruction can ensue with reduced computing power and/or resolution and/or as a partial rotation reconstruction.

As an alternative to the determination of rest phases and movement phases using movement artifacts, a signal can be detected, at the same time as the acquisition of a the projections for the image generation, that represents a physiological function reflecting the periodic motion. The analysis of the projection data (as to whether they were acquired during a rest phase or a movement phase of a region of interest of the organ) ensues by a temporal association of the data with the time curve of the signal representing the physiological function. Data acquired during a rest phase of a particular region of interest of the organ that was acquired during a time interval in which the curve of the signal indicates that the respective region of interest is in a rest phase. Thus, using the signal representing the physiological function, data are subsequently selected that represent the respective region of interest in a rest phase, and only such data is used for image reconstruction.

For the generation of computed tomography images of the heart, in an embodiment of the invention the ECG of the organism is acquired during the acquisition of the projections, and with regard to each region of interest of the heart at least one useable time interval is respectively identified between two successive R-waves of the ECG. Data acquired during a rest phase of the respective region of interest of the heart, which were acquired during the usable time interval, are used for image reconstruction.

Since the period duration of the cardiac activity is not constant, in an embodiment of the invention a time interval is identified as a usable time interval that contains a predetermined first fraction of a heart period (cycle) after the R-wave of the ECG commencing the respective heart cycle, and a duration that is equal to a second predetermined fraction of the respective heart period.

In order to charge the patient with as minimal a radiation dose as possible, in an embodiment of the invention a threshold criterion is predetermined for the signal which, when satisfied, indicates that a respective region of interest of the organ is in a rest phase. To acquire the projections required for the generation of an image, the x-ray source is activated only during such time segments during which the threshold criterion is satisfied.

A further object of the invention is to provide a computed tomography device operating according to the above-described method. Thus a user can select from a number test images that are lacking in movement artifacts. On the basis of the test images thus selected, the computed tomography device identifies at least one usable time interval wherein the data were acquired during a rest phase and then only that data are used for the image reconstruction.

DESCRIPTION OF THE DRAWINGS

FIG. 9 is schematic block diagram of a computed tomography device to implement the inventive method.

DESCRIPTION OF THE PREFERRED EMBODIMENTS

Figure 1:
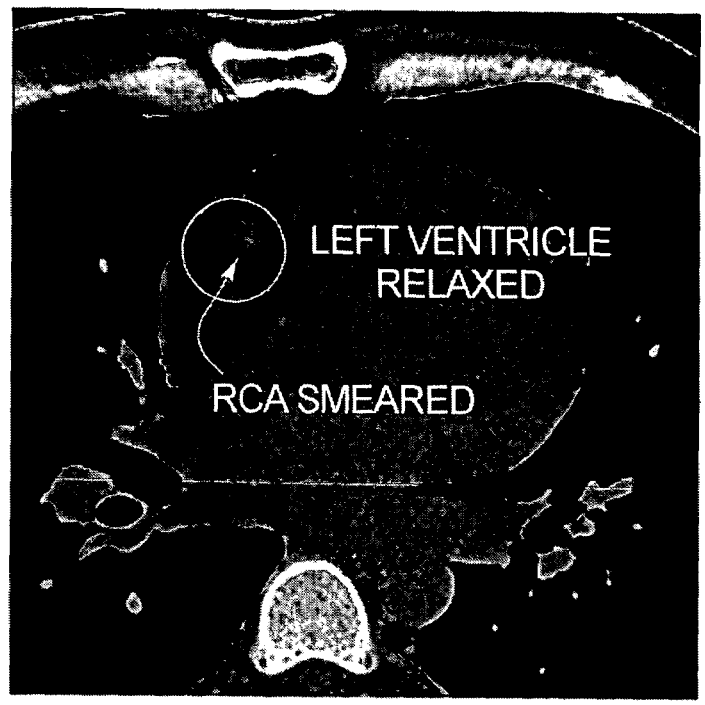
FIG. 1 and 2 are two computed tomography images showing the rest phases of different regions of the heart.
Figure 2:
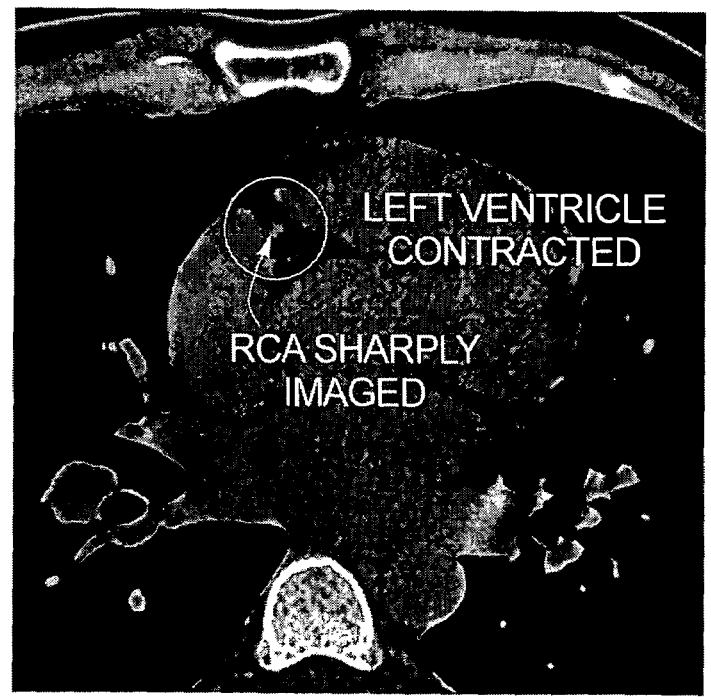
Figure 3:
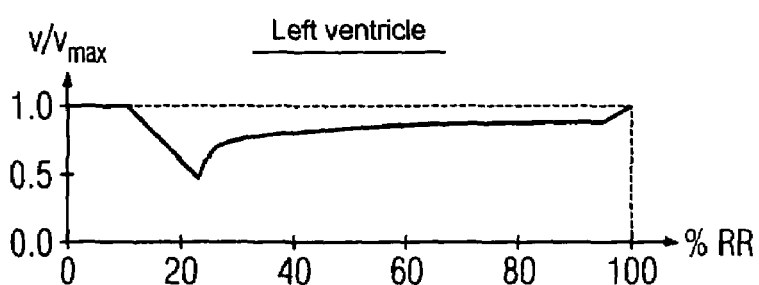
FIG. 3 through 7 illustrate of the movement speed of different regions of the heart during a heart cycle, in the form of time curves.
Figure 4:
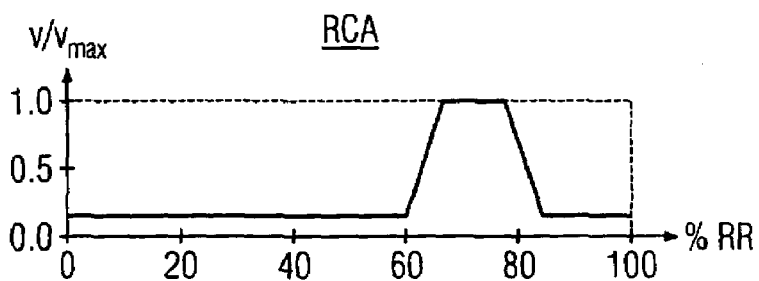
Figure 5:
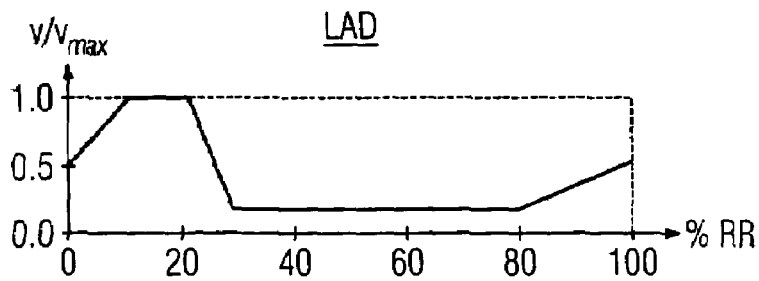
Figure 6:
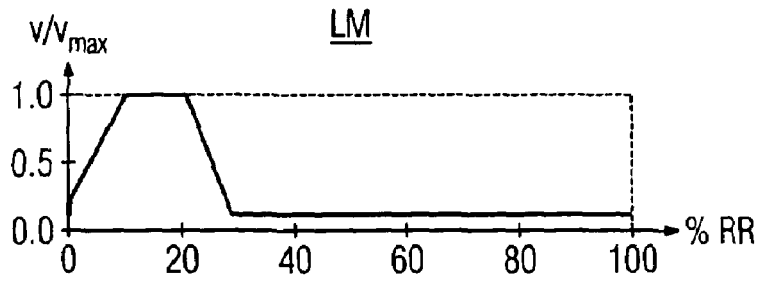
Figure 7:
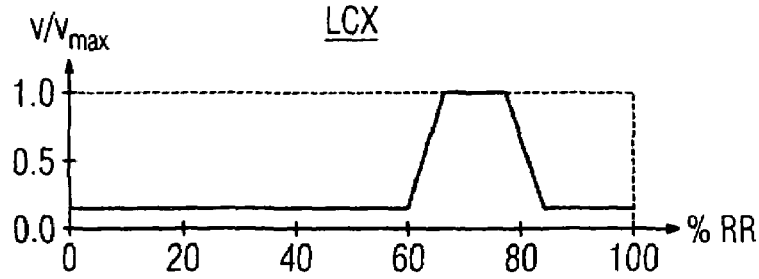

As shown in FIG. 1 and 2, the spatial motion of the coronary arteries and the heart ventricles vary in speed and phase in the slice plane under consideration during a heart cycle. FIGS. 1 and 2 show the same slice place of a heart, however the data respectively forming the basis of FIGS. 1 and 2 were acquired during different time periods within a heart cycle. FIG. 1 thus shows the diastolic rest phase that begins after approximately 30% of the total duration of a heart cycle and ends after approximately 70% of the total duration of a heart phase (30%–70%-R interval). FIG. 2 shows the systolic contraction phase (80%–120%-RR interval). Both images were reconstructed with 250 ms time resolution.

It can be clearly recognized from using FIG. 1 that in diastole the entire heart is sharply visible in the region of the left ventricle, while the depiction of the RCA is severely impaired by conditional smearing arising due to motion.

In contrast, the image reconstructed in systole according to FIG. 2 shows the RCA sharply and the region around the left ventricle is in contrast shown with movement artifacts.

It is thus evident that the left ventricle and RCA move out of phase. This conclusion is valid as well for other coronary arteries, whereby CX and RCA move substantially in phase, while LM and LAD move approximately in phase with the left ventricle.

This is once again illustrated in FIGS. 3 through 7 that, in the form of time diagrams, show the movement speed of different regions of the heart during a heart cycle, thus during the time period between two successive R-waves of the ECG, whereby the ratio of momentary and maximal movement speed of the respective region is applied over the duration of a heart cycle specified in percent.

For artifact-free depiction of all regions of interest, according to the FIGS. 3 through 7 only the phase 30% RR through 60% RR should be considered, but, in particular for higher pulse rates, this is not sufficient to acquire all projections necessary to reconstruct a CT (computed tomography) image.

According the inventive method, it is not attempted to image all regions of interest of the heart during a single measurement interval. Instead, multiple projections are acquired during at least one rotation of the x-ray source around the heart and during a time duration that is at least equal to one period of the heart cycle, the projection data are analyzed as to whether the data were acquired during a rest phase or movement phase of a respective region of interest of the heart, and an image of the organ is reconstructed using only data acquired during a rest phase of a respective region of interest of the organ.

Figure 8:
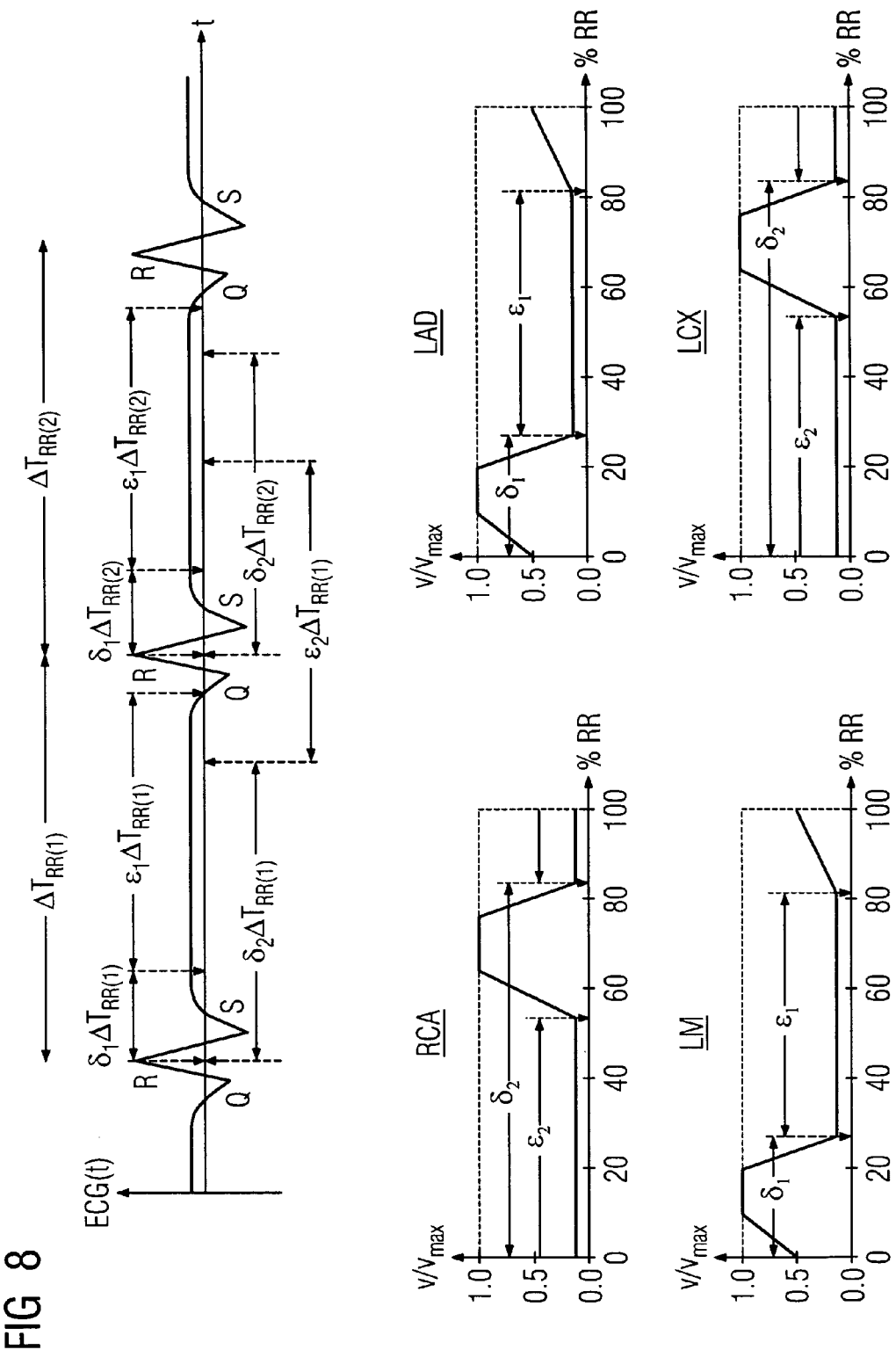
FIG. 8 shows the curve of the ECG signal of a patient and the reconstruction phase suitable for the different regions of the heart according to the FIGS. 4 through 8.

As is shown in FIG. 8, two different intervals ($\delta_1,\epsilon_1$) for LAD and LM as well as ($67_2,\epsilon_2$) for RCA and LCX are used for image reconstruction. $\delta_n$ defines the start point, dependent on the occurrence of the R-wave initiating a heart cycle, $\epsilon_n$ defines the duration of the interval of an RR cycle dependent on the duration $\Delta T_{RR}$.

A computed tomography device to implement the above-described method is schematically shown in FIG. 9.

The computed tomography device has a measuring unit formed by from an x-ray source 1 that emits an x-ray beam 2 and a detector 3 which having one or more successive lines of individual detectors in the z-direction, for example 512 individual detectors per line. The focus of the x-ray source 1 from which the x-ray beam 2 originates is indicated with 4. Dependent on whether one or more lines of individual detectors is used, the x-ray beam is gated so as to be fan-shaped or pyramid-shaped or conical by means of a primary beam diaphragm.

The examination subject (in the case of the shown exemplary embodiment a human patient 5) lies on a positioning table 6 that extends through the measuring opening 7 of a gantry 8.

The x-ray source 1 and the detector 3 are mounted opposite one another on the gantry 8. The gantry is centered the z-axis (indicated with z, proceeding at a right-angle to the plane FIG. 9) of the computed tomography device that also is the system axis. The gantry is rotated around the z-axis by a motor 13 to scan the patient 5 in the α-direction indicated by the arrow α. This rotation proceeds through an angle that is at least equal to 180° (π) plus fan angle (aperture angle of the fan-shaped x-ray beam 2). The x-ray beam 2 originating from an x-ray source 1, which is supplied with voltage by a generator 9, irradiates a measuring field of circular cross section. The focus 4 of the x-ray source 1 move on a circular curved focus path 15 around the rotational center lying on the z-axis.

At predetermined angle positions of the measuring unit 1, 3 (known as projection angles), measurement values (datasets) are acquired in the form of known as projections. The corresponding measurement data are supplied from the detector 3 to an electronic computer 11 which reconstructs the attenuation coefficients of the pixels of a pixel matrix from the projections and visually reproduces the pixel values on a display device, for example a monitor 12, on which images of the slices of the patient 5 irradiated in the projections thus appear.

When the detector 3 has multiple lines of detector elements, if required multiple slices of the patient 5 can be acquired simultaneously. In this case, per projection angle, a number of projections corresponding to the number of the active detector lines is acquired.

A spiral scan can be implemented if the motor 13 associated with the gantry 8 is not only able to produce for a partial rotation or a complete rotation of the gantry 8, but is in addition suitable to continuously rotate the gantry 8, and with a relative motion of the positioning table 6 in the z-direction, and thus a relative motion of the examination subject 5 with respect to the gantry 8 and the x-ray source 1 and detector 3.

To implement examinations of the heart or heart-proximal regions of the body of the patient 5 moving in the rhythm of the heart action, the computed tomography device has, according to FIG. 1 a known electrocardiograph unit 17 (ECG unit) that can be connected with the patient 5 via electrodes (of which one is shown in FIG. 1 and is indicated with 18) and serves to detect the ECG signal of the patient 5 in parallel with the examination by the computed tomography device. The ECG data, preferably in digital form, are supplied to the computer 11.

The electrodes of the electrocardiograph 17 are, as much as is possible, applied to the body of the patient 5 such that they do not affect the irradiation of the patient 5.

A keyboard 19 and a mouse 20 that enable operation of the computed tomography device are connected to the computer 11. Moreover, a further monitor 21, on which the ECG of the patient 5 can be shown, is connected to the computer 11.

In a first type of operation of the CT device based on the inventive method, an operator marks on the monitor 21, by means of the mouse 20, the region of a period of the ECG that corresponds to the rest phase of the region of the heart that should be shown in the computed tomography images.

Thus in the ECG of the patient 5, with regard to the respective region of interest of the heart 1, a useable time interval lying between two successive R-waves of the ECG is marked, and the computer 11 uses only data for the image reconstruction that were acquired in the individual heart cycles respectively during the useable time interval. The computer 11 considers that data as having been acquired during a rest phase.

The computer 11 identifies the position and duration of a time interval (marked as a useable time interval by the mouse 20 on the monitor 21) within a heart period, by a first fraction of the respective heart period that elapses after the R-wave commencing the heart cycle and the beginning of the usable time interval, and by second fraction of the duration of the heart cycle that follows the first fraction and corresponds to the duration of the usable time interval.

In this manner, it is also possible, given fluctuations of the heart period, to analyze data corresponding to the acquired projections as to whether the data were acquired during a rest phase or movement phase of the respective region of interest of the heart. The computer 11 then considers that data that was acquired during usable time intervals as data acquired during a rest phase, and subsequently uses only that data to reconstruct the computed tomography image.

In an alternative operational mode of the computed tomography device, the analysis of the data corresponding to the projections (as to whether they were acquired during a rest phase or a movement phase of the respective region of interest of the heart) is based on the detection of movement artifacts in test images.

In this mode a number of temporally quickly successive test images is reconstructed from the available data, and these test images that are analyzed for movement artifacts.

This can ensue by computer 11 examining the test images for the existence of line artifacts and/or double contours, and considers the existence of line artifacts and/or double contours as an indication of movement artifacts.

The computer 11 then considers the data that produced a test image that is substantially free of movement artifacts in at least the image region showing the respective region of interest of the heart, as acquired during a rest phase of the respective region of interest of the heart and uses such data exclusively for the actual image reconstruction.

In a modification of the second operational mode, the computer 11 detects movement artifacts using difference images acquired by subtraction of successive test images. A difference image that (theoretically) contains no image information at all indicates an absence of movement artifacts.

In order to reduce the time for reconstruction of the test images, the computer 11 can undertake the reconstruction of the test images with reduced computing power and/or reduced resolution and/or as a partial rotation reconstruction.

In a third operational mode similar to the second operational mode, the computer 11 reconstructs the test images not from the same data that also will be used of the reconstruction of the actual images, but rather from data that are acquired during a test mode that precedes the acquisition mode.

During such a test mode (that should if at all possible immediately precede the acquisition mode), projections are acquired with simultaneous recording of the ECG from which test images are reconstructed that are shown on the monitor 12. An operator evaluates these images and indicates by means of the mouse 20 those images that he or she recognizes as lacking movement artifacts with regard to the respective region of interest of the heart. Based on the temporal position of the test images so indicated relative to the ECG, the computer 11 determines (with consideration of the ECG signal) a useable time interval (with regard to the respective region of interest). The position and duration of this time interval, as already specified, can be defined by a first fraction and a second fraction of the heart period, and indicates the rest phase of the respective region of interest.

In the subsequent acquisition modes, the projections serving for the actual image generation are acquired, from which the computer 11 uses, for the reconstruction of the respective region of interest, only projections that are acquired during a (as specified) useable time interval determined on the basis of the test images, and thus during a rest phase of the respective region of interest.

In order to avoid exposing the patient to unnecessary x-ray dosage, in all specified operational modes the computer 11, dependent on the ECG signal, can activate the x-ray source 1 only when the likelihood actually exists that the respective region of interest is in a rest phase.

For this purpose, the computer 11 compares the ECG signal with a threshold and controls the voltage generator 9 such that the x-ray source 1 is activated only when the threshold is not satisfied.

In the case of all operating modes, in addition the possibility exists to analyze the data with regard to a number of regions of the heart as to whether the data were acquired during a rest phase or during a movement phase of the respective region of interest, with the result that, for example with regard to first and second interest regions, computed tomography images can be reconstructed that are based only on such data that were acquired during a rest phase of the first or second region of interest of the heart. Both computed tomography images can then be merged into a single image that shows both the first and the second regions of interest in their respective rest phases.

For this purpose, the computer 11 can show, for example, both images on the monitor 12, such that an operator can mark by means of the mouse 20 those regions of both images that should be merged into a common image, whereupon the computer 11 shows the merged image.

Naturally, these procedures can be applied for more than two regions of interest.

The invention has been described in the context of an example for examinations of the heart; however, it can also be used in the examination of another periodically moving organ of an organism, whereby the term organ should be understood as encompassing a region of the body.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a computed tomography image of a periodically moving organ of an organism, wherein the organ comprises a plurality of different regions each having a rest phase and a movement phase, with the respective rest phases of different ones of said regions ensuing at different points in time, comprising the steps of:

(a) emitting an x-ray beam from a focus of an x-ray source and rotating at least said focus around said organ to irradiate said organ from a plurality of different directions, and detecting x-rays in said x-ray beam attenuated by said organ at each of said directions, to obtain a plurality of sets of projection data of said organ in rapid succession, each set of projection data representing a test image of said organ, during at least one rotation of said focus around said organ and during a duration that is at least equal to one period of the periodic movement of the organ;

(b) analyzing said sets of projection data to determine whether the projection data in each test image were acquired during a rest phase or during a movement phase of only one of said regions of said organ by detecting movement artifacts in an image region of each test image containing said one region of said organ, and designating projection data in respective test images that are free of movement artifacts as having been acquired during the rest phase of said one of said regions; and (c) reconstructing a diagnostic image of said organ using only projection data from said test images acquired during the respective rest phase of said one of said regions of said organ.

2. A method as claimed in claim 1 wherein step (b) comprising comprises separately analyzing said projection data with regard to each of a plurality of said regions of said organ to determine whether the projection data were acquired during the respective rest phase or the respective movement phase of each of said plurality of regions, and wherein step (c) comprises reconstructing a single image of said organ using only projection data acquired during the respective rest phase of each of said regions.

3. A method as claimed in claim 1 comprising detecting movement artifacts by detecting at least one of line artifacts and double contours in the respective test images.

4. A method as claimed in claim 1 comprising detecting movement artifacts by forming respective difference images from respective pairs of successive test images.

5. A method as claimed in claim 1 comprising generating said test images with a computing power that is reduced compared to a computing power used to reconstruct said image of said organ in step (c).

6. A method as claimed in claim 1 comprising acquiring said test images with a reduced resolution in comparison to a resolution of said image of said organ reconstructed in step (c).

7. A method as claimed in claim 1 comprising acquiring said test images during only a partial rotation of said focus around said organ.

8. A method for generating a computed tomography image of a periodically moving organism of an organism, wherein the organ comprises a plurality of different regions each having a rest phase and a movement phase, with the respective rest phases of different ones of said regions ensuing at different points in time, comprising the steps of:

(a) emitting an x-ray beam from a focus of an x-ray source and rotating at least said focus around said organ to irradiate said organ from a plurality of different directions, and detecting x-rays in said x-ray beam attenuated by said organ at each of said directions, to obtain a plurality of sets of projection data of said organ in rapid succession, each set of projection data representing a test image of said organ, during at least one rotation of said focus around said organ and during a duration that is at least equal to one period of the periodic movement of the organ, each of said projections comprising projection data and in parallel with the acquisition of said projections, acquiring a signal from said organ representing a physiological function of said organ, said signal reflecting said periodic movement of said organ;

(b) analyzing said sets of projection data to determine whether the projection data were acquired during a rest phase or during a movement phase of one of said regions of said organ, identifying a time interval in said signal corresponding to the respective rest phase of said one of said regions, and identifying projection data for said region obtained during said time interval; and (c) reconstructing a diagnostic image of said organ using only projection data acquired during the respective rest phase of said one of said regions of said organ.

9. A method as claimed in claim 8 wherein said organ is a heart, and comprising acquiring an ECG as said signal.

10. A method as claimed in claim 9 comprising identifying said time interval occurring between two successive R-waves of said ECG.

11. A method as claimed in claim 10 comprising identifying said interval by identifying a predetermined first fraction of a period of the heart following a first of said two successive R-waves, and identifying said interval as a duration equal to a second predetermined fraction of said period following said first predetermined fraction.

12. A method as claimed in claim 8 comprising comparing said signal to a threshold criterion and activating said x-ray source to emit said x-ray beam to acquire said projections only during time segments wherein said threshold criterion is satisfied.

13. A computed tomography apparatus for generating an image of a periodically moving organ of an organism, said organ comprising a plurality of different regions each having a rest phase and a movement phase, with the respective rest phases of different regions of said organ ensuing at different points in time, said computed tomography apparatus comprising:

an x-ray source having a focus from which an x-ray beam is emitted;

a radiation detector on which said x-ray beam is incident;

at least said focus of said x-ray source being rotatable around said organism to irradiate said organ in said organism from a plurality of different directions, and said radiation detector detecting radiation in said x-ray beam attenuated by said organ at each of said directions, to obtain a plurality of sets of projection data of said organ in rapid succession, each set of projection data representing a test image of said organ, during at least one rotation of said focus around said organism and during a duration at least equal to a period of said movement of said organ; and a computer supplied with said projection data, said computer analyzing said sets of projection data to determine whether said projection data in each set were acquired during a respective rest phase of one of said regions of said organ by detecting movement artifacts in an image region of each test image containing said one region of said organ, and designating projection data in respective test images that are free of movement artifacts as having been acquired during the rest phase of said one of said regions, and reconstructing a diagnostic image of the organ using only projection data from said test images acquired during said respective rest phase of said one of said regions.

14. A computed tomography apparatus as claimed in claim 13 wherein said organ is the heart of said organism, and further comprising an ECG unit adapted to interact with the heart to obtain an ECG signal therefrom in parallel with said projections, said ECG unit supplying said ECG signal to said computer and said computer identifying a time interval from said ECG signal corresponding to said respective rest phase of said one of said regions, and said computer using only projection data obtain during said interval for reconstructing said image of the heart.

15. A computed tomography apparatus for generating an image of a periodically moving organ of an organism, said organ comprising a plurality of different regions each having a rest phase and a movement phase, with the respective rest phases of different regions of said organ ensuing at different points in time, said computed tomography apparatus comprising:

an x-ray source having a focus from which an x-ray beam is emitted;

a radiation detector on which said x-ray beam is incident;

at least said focus of said x-ray source being rotatable around said organism to irradiate said organ in said organism from a plurality of different directions, and said radiation detector detecting radiation in said x-ray beam attenuated by said organ at each of said directions, thereby producing a plurality of projections, during at least one rotation of said focus around said organism and during a duration at least equal to a period of said movement of said organ, each of said projections comprising projection data in parallel with the acquisition of said projections, acquiring a signal from said organ representing a physiological function of said organ, said signal reflecting said periodic movement of said organ; and a computer supplied with said projection data, said computer analyzing said projection data to determine whether said projection data in each set were acquired during a respective rest phase of one of said regions of said organ, and reconstructing an image of the organ using only projection data from said respective rest phase of said one of said regions identifying a time interval in said signal corresponding to the respective rest phase of said one of said regions, and identifying projection data for said region obtained during said time interval.

16. A computed tomography apparatus as claimed in claim 15 wherein said organ is the heart of said organism, and further comprising an ECG unit adapted to interact with the heart to obtain an ECG signal therefrom in parallel with said projections, said ECG unit supplying said ECG signal to said computer and said computer identifying a time interval from said ECG signal corresponding to said respective rest phase of said one of said regions, and said computer using only projection data obtain during said interval for reconstructing said image of the heart.

* * * * *